(12) United States Patent
Tokudome

(10) Patent No.: US 12,329,579 B2
(45) Date of Patent: Jun. 17, 2025

(54) ULTRASOUND DIAGNOSTIC APPARATUS CONFIGURED TO MODIFY EXAMINATION PROTOCOL

(71) Applicant: FUJIFILM Healthcare Corporation, Kashiwa (JP)

(72) Inventor: Wataru Tokudome, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 226 days.

(21) Appl. No.: 18/106,902

(22) Filed: Feb. 7, 2023

(65) Prior Publication Data

US 2023/0270411 A1    Aug. 31, 2023

(30) Foreign Application Priority Data

Feb. 25, 2022   (JP) ................... 2022-028324

(51) Int. Cl.
*A61B 8/00* (2006.01)
*G06T 7/00* (2017.01)

(52) U.S. Cl.
CPC .............. *A61B 8/465* (2013.01); *A61B 8/463* (2013.01); *A61B 8/469* (2013.01); *G06T 7/0012* (2013.01); *G06T 2200/24* (2013.01); *G06T 2207/10132* (2013.01); *G06T 2207/30096* (2013.01)

(58) Field of Classification Search
CPC ............................... A61B 8/465; A61B 8/469
See application file for complete search history.

(56) References Cited

U.S. PATENT DOCUMENTS

| | | | | |
|---|---|---|---|---|
| 6,458,081 B1* | 10/2002 | Matsui | .......... | A61B 8/463 600/437 |
| 2011/0131528 A1* | 6/2011 | Nakamura | ........ | A61B 6/563 715/810 |
| 2015/0366534 A1* | 12/2015 | Nair | ........... | A61B 8/0891 600/463 |
| 2017/0235903 A1* | 8/2017 | McLaughlin | ..... | G01S 7/52084 715/708 |
| 2018/0068079 A1* | 3/2018 | Bronkalla | ......... | G16H 10/20 |
| 2018/0092629 A1* | 4/2018 | Yoneyama | ......... | A61B 8/06 |
| 2021/0015447 A1* | 1/2021 | St. Pierre | ......... | A61B 10/0233 |

(Continued)

FOREIGN PATENT DOCUMENTS

| | | |
|---|---|---|
| CN | 113749686 A | 12/2021 |
| JP | 2017-505204 A | 2/2017 |

(Continued)

OTHER PUBLICATIONS

Feb. 4, 2025 Japanese official action (and English-language translation thereof) in connection with Japanese Patent Application No. 2022-028324.

*Primary Examiner* — Jeffrey G Hoekstra
*Assistant Examiner* — Nyrobi Celestine
(74) *Attorney, Agent, or Firm* — Paul Teng

(57) ABSTRACT

A detector detects a lesion site contained in an ultrasound image while an examination protocol is running. A display processor (display controller) displays an option list in response to detection of the lesion site. A protocol modifying unit incorporates a specific option selected from the option list into the examination protocol being run. A protocol execution controller controls operations of an ultrasound diagnostic apparatus in accordance with a modified examination protocol in which the specific option is incorporated.

12 Claims, 13 Drawing Sheets

(56) References Cited

U.S. PATENT DOCUMENTS

| | | | |
|---|---|---|---|
| 2021/0052253 A1 | 2/2021 | Cadieu et al. | |
| 2021/0059631 A1* | 3/2021 | Lewis | G06F 21/84 |
| 2021/0280298 A1* | 9/2021 | Samset | A61B 5/055 |
| 2022/0027024 A1* | 1/2022 | Gulaka | G06T 11/003 |

FOREIGN PATENT DOCUMENTS

| | | |
|---|---|---|
| JP | 6130572 B | 5/2017 |
| JP | 2020-141883 A | 9/2020 |
| JP | 2021-520939 A | 8/2021 |

* cited by examiner

FIG. 2

Table 44A:

| ID | PROTOCOL NAME | No. | STEP NAME | OPERATING CONDITIONS | ... |
|---|---|---|---|---|---|
| ** |  | 1 | *** | ,*,...,**** | ... |
| | | 2 | ***** | ,*,...,**** | ... |
| | | 3 | ***** | ,*,...,**** | ... |
| | | 4 | ***** | ,*,...,**** | ... |
| | | ... | ... | ... | ... |
| | | m | ***** | ,*,...,**** | ... |

FIG. 3

Table 46A:

| ID | OPTION NAME | No. | STEP NAME | OPERATING CONDITIONS | ... |
|---|---|---|---|---|---|
| ** |  | 1 | *** | ,*,...,**** | ... |
| | | 2 | ***** | ,*,...,**** | ... |
| | | 3 | ***** | ,*,...,**** | ... |
| | | 4 | ***** | ,*,...,**** | ... |

FIG. 4

Table 48:

| PROTOCOL ID | MEDICAL DIVISION (EXAMINATION SITE) | ... |
|---|---|---|
| 001 | **** | ... |
| 002 | **** | ... |
| 003 | **** | ... |
| ... | ... | ... |

FIG. 5

Table 50:

| OPTION ID | MEDICAL DIVISION (EXAMINATION SITE) | TYPE OF LESION SITE | ... |
|---|---|---|---|
| 001 | **** | **** | ... |
| 002 | ** | ,** | ... |
| 003 | ** | ,,** | ... |
| ... | ... | ... | ... |

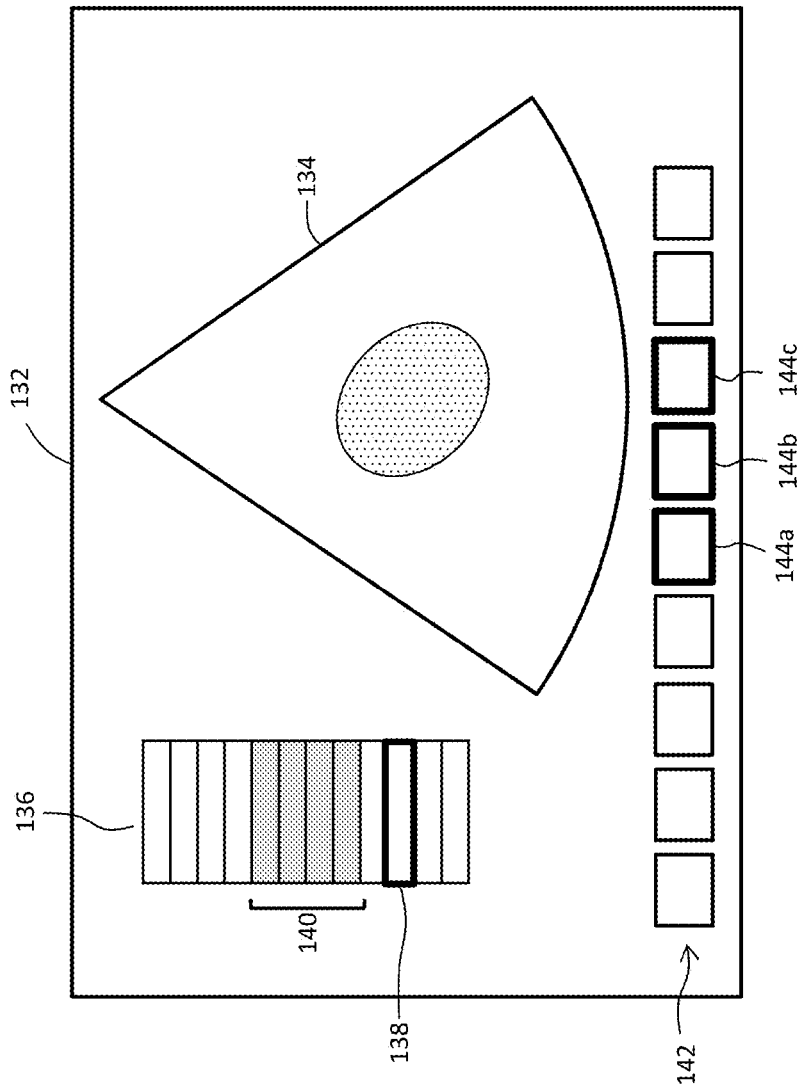

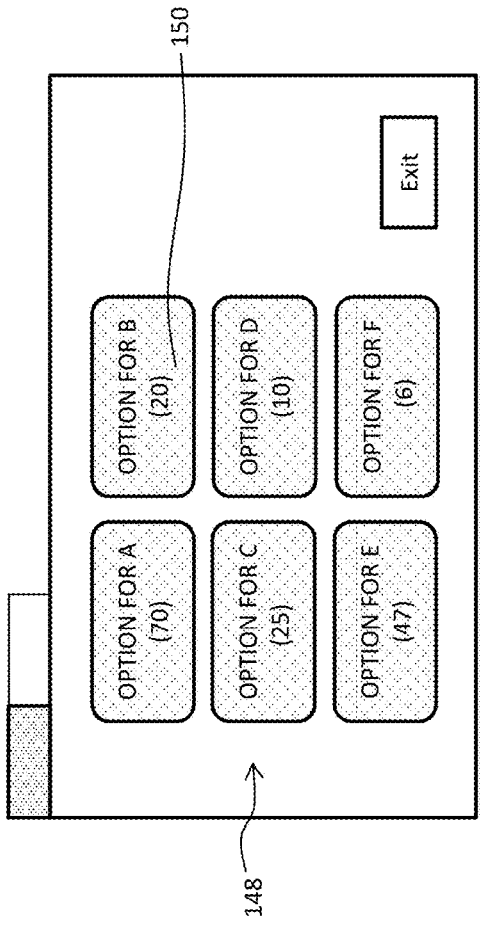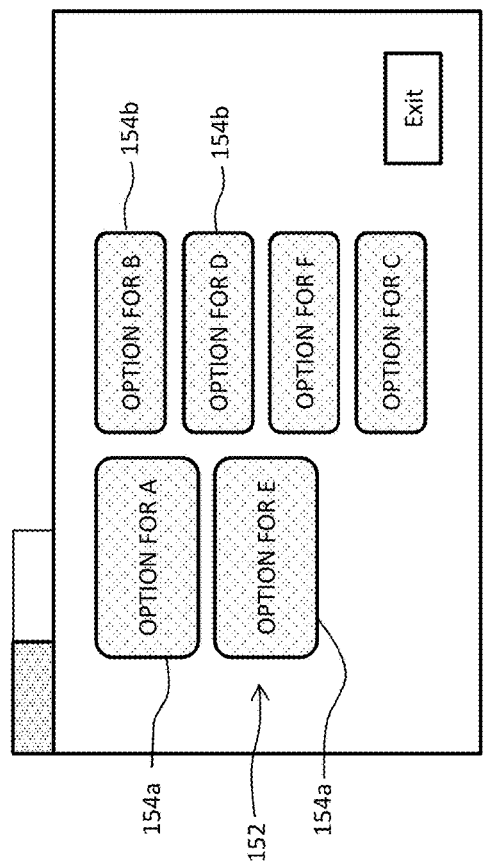

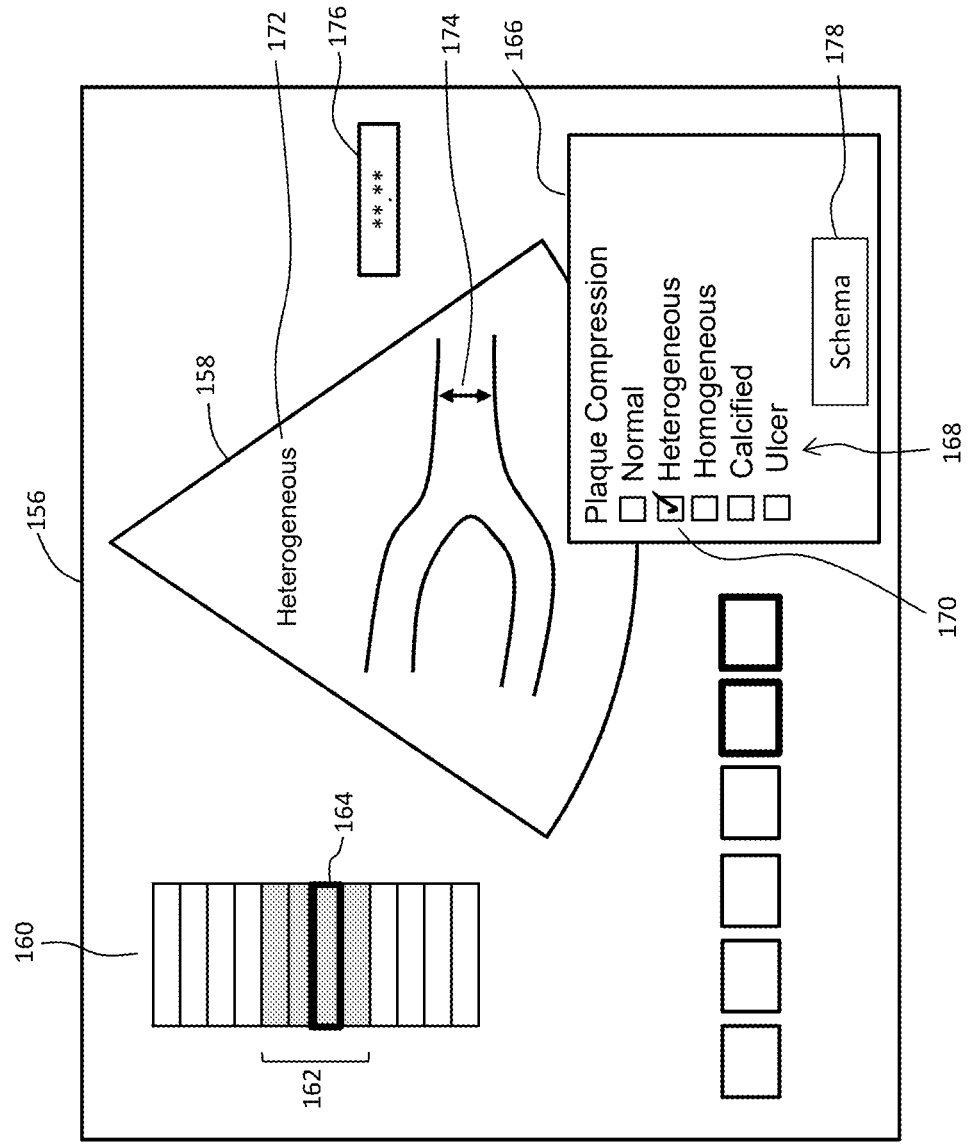

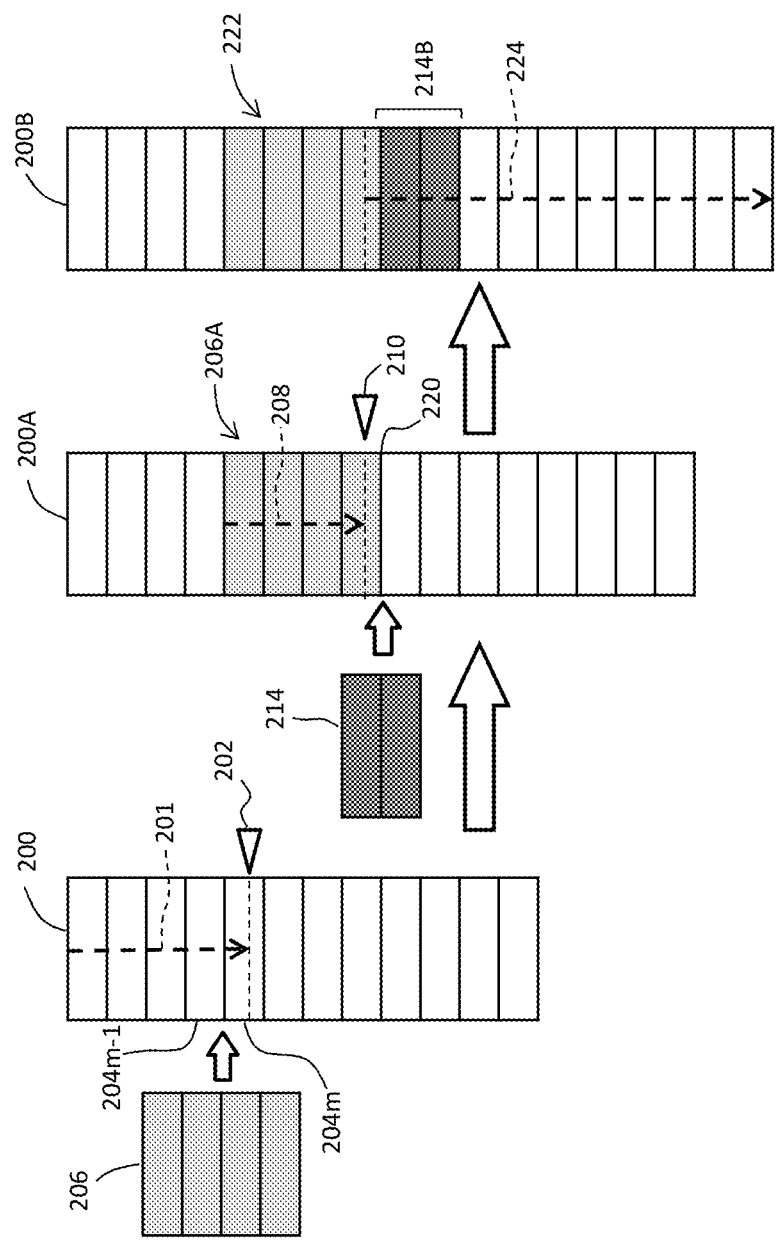

ULTRASOUND DIAGNOSTIC APPARATUS CONFIGURED TO MODIFY EXAMINATION PROTOCOL

CROSS REFERENCE TO RELATED APPLICATION

This application claims priority to Japanese Patent Application No. 2022-028324 filed on Feb. 25, 2022, which is incorporated herein by reference in its entirety including the specification, claims, drawings, and abstract.

TECHNICAL FIELD

The present disclosure relates to an ultrasound diagnostic apparatus, and in particular relates to an ultrasound diagnostic apparatus having a function to execute an examination protocol.

BACKGROUND

Ultrasound diagnostic apparatuses generally have a function of executing an examination protocol as an ultrasound examination supporting function (see JP 6130572 B, for example). The examination protocol is composed of a plurality of steps arranged in a time sequential order. In general, operating conditions including an ultrasound diagnostic mode (operating mode) are automatically established at a start time of executing each of the steps. When a predetermined operation (such as an operation to store an image, or an operation to unfreeze an image, for example) is performed in a final stage of each of the steps, transition to a next step is automatically performed. The plurality of steps constituting the examination protocol may include steps accompanying a measurement. In the step accompanying a measurement, a measuring operation (such as a distance measurement or an area computation) is performed on the basis of an ultrasound image prior to the operation to store the ultrasound image. With the function of executing an examination protocol, a series of steps can be reliably completed without omitting any step, and the burdens on a user can be significantly reduced accordingly.

Patent publication JP 2020-141883 A discloses an ultrasound diagnostic apparatus having a function of executing an examination protocol. In the ultrasound diagnostic apparatus, a branch protocol is executed when a predetermined condition is satisfied in the course of processing in any one of steps constituting the examination protocol. The patent publication is silent about any one of operations to modify the examination protocol based on a result of image analysis, select a branching position, or modify representation of the examination protocol.

In a case where a lesion site appears in an ultrasound image while an examination protocol is executed, it is generally required that a close investigation of the lesion site be conducted. In this case, if a user is requested to perform setting or an operation necessary for closely observing the lesion site while suspending the examination protocol having been executed, a significant burden will be placed on the user. Also, in that case, a possibility that acquisition of a necessary image may be accidentally omitted is increased. In light of continuous support for user operation, it is desired that at the occurrence of a lesion site, contents of the examination protocol be modified based on the lesion site in an additional or expansive manner.

An object of the present disclosure is to provide an ultrasound diagnostic apparatus in which when a lesion site emerges, contents of an examination protocol can be modified easily and suitably with respect to the lesion site.

SUMMARY

An ultrasound diagnostic apparatus according to an aspect of the present disclosure includes a protocol execution controller configured to control a series of operations in accordance with an examination protocol composed of a plurality of steps, the series of operations including operations from transmission and reception of an ultrasound wave to display of an ultrasound image; a detector configured to detect a lesion site contained in the ultrasound image while the examination protocol is running; a display controller configured to display, in response to detection of the lesion site, an option list showing one or more options; and a protocol modifying unit configured to incorporate a specific option selected from the option list into the examination protocol being running, in which each of the one or more options is composed of one or more additional steps. In the ultrasound diagnostic apparatus, after the specific option is incorporated, the protocol execution controller controls the series of operations in accordance with a modified examination protocol in which the specific option is incorporated.

A program according to another aspect of the present disclosure is executed in an ultrasound diagnostic apparatus in which a series of operations are controlled in accordance with an examination protocol composed of a plurality of steps, the series of operations including operations from transmission and reception of an ultrasound wave to display of an ultrasound image, and the program includes a function of detecting a lesion site contained in the ultrasound image while the examination protocol is running, a function of displaying a option list showing one or more options in response to detection of the lesion site, and a function of incorporating a specific option selected from the option list into the examination protocol being running, in which each of the one or more options is composed of one or more additional steps. In the ultrasound diagnostic apparatus, after the specific option is incorporated, the series of operations are controlled in accordance with a modified examination protocol in which the specific option is incorporated.

BRIEF DESCRIPTION OF DRAWINGS

Embodiments of the present disclosure will be described based on the following figures, wherein:

FIG. 2 shows an example of protocol information;

FIG. 3 shows an example of option information;

FIG. 4 shows an example of a protocol managing table;

FIG. 5 shows an example of an option managing table;

FIG. 9 shows a second display example;

FIG. 10 shows a second example of the option list;

FIG. 11 shows a third example of the option list;

FIG. 12 shows a display image containing a list of findings;

FIG. 16 shows a second example of the option inserting method.

DESCRIPTION OF EMBODIMENTS

Figure 1:
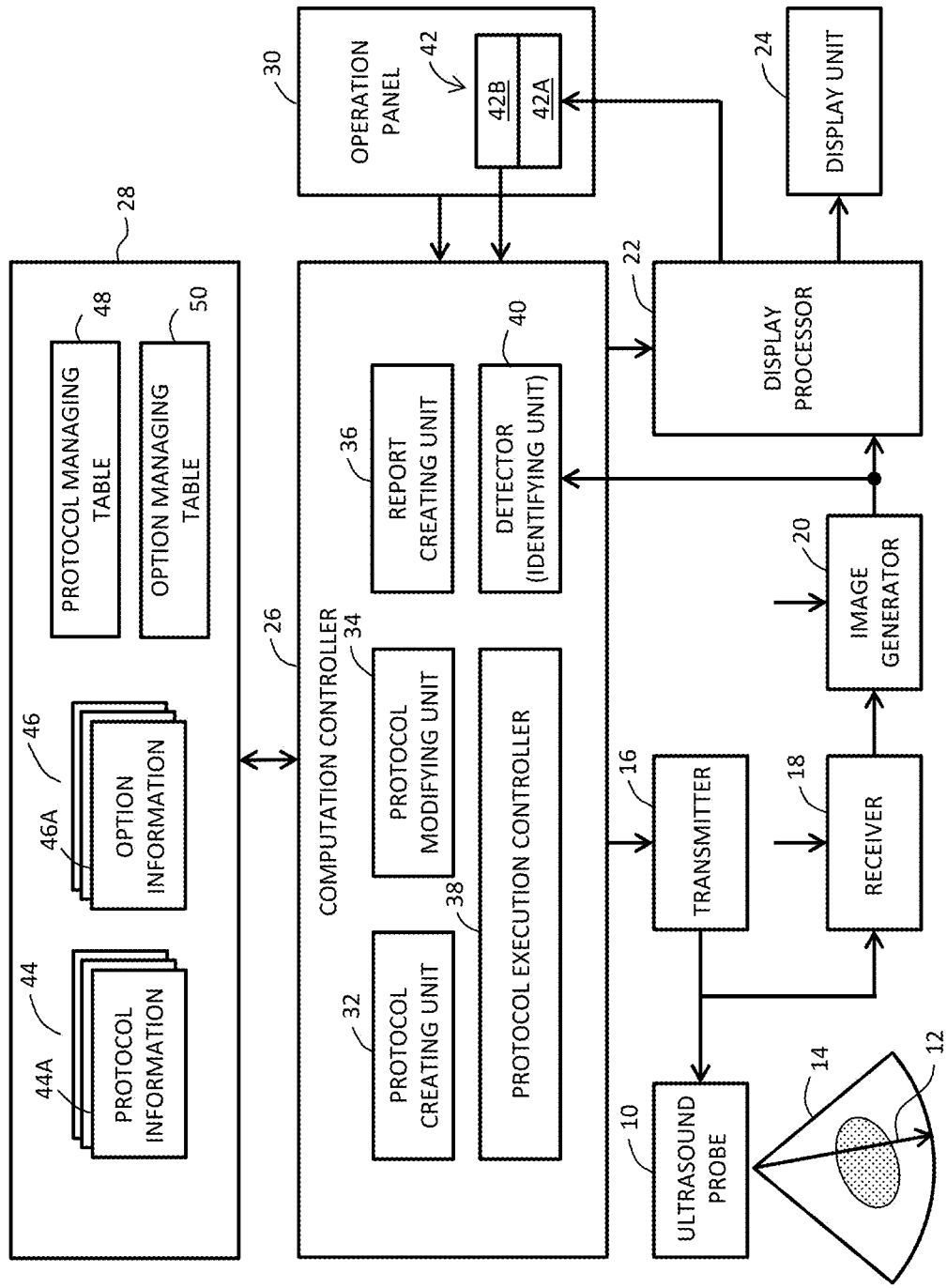
FIG. 1 is a block diagram showing a configuration example of an ultrasound diagnostic apparatus according to an embodiment.

Hereinafter, embodiments will be described with reference to the drawings.

1. Overview of Embodiment

An ultrasound diagnostic apparatus according to an embodiment includes a protocol execution controller, a detector, a display controller, and a protocol modifying unit. The protocol execution controller controls a series of operations (apparatus operations) including operations from transmission and reception of ultrasound waves to display of an ultrasound image in accordance with an examination protocol composed of a plurality of steps. The detector detects a lesion site contained in the ultrasound image while the examination protocol is running. The display controller displays an option list showing one or more options in response to detection of the lesion site. The protocol modifying unit incorporates a specific option selected from the option list into the examination protocol being running. Each of the options is composed of one or more additional steps. After the specific option is incorporated, the protocol execution controller controls the series of operations in accordance with a modified examination protocol in which the specific option is incorporated. A processor, which will be described below, functions as the protocol execution controller, the detector, the display controller, and the protocol modifying unit.

According to the above-described configuration, when a lesion site is detected while the examination protocol is running, the option list is displayed automatically or through an operation by a user. From the displayed option list, the user selects a specific option that fits the detected lesion site. Then, the selected specific option is incorporated into the examination protocol being running. In other words, the examination protocol is automatically modified in real time. Therefore, according to the above-described configuration, contents of the examination protocol can be fitted to the lesion site that has emerged, without placing a heavy burden on the user.

In an embodiment, the protocol modifying unit identifies, as a reference step, a step that is in progress when the lesion site is detected, and determines a position immediately before or immediately after the reference step as an option inserting position in the running examination protocol.

In general, the lesion site is detected while a certain step is in progress. Assuming that an option is inserted at some point into the certain step, the certain step will be divided into two sections by the inserted option, which may, depending on situation, incur a problem of user confusion or a problem in that the certain step is not entirely completed. However, such problems can be easily evaded by inserting the option immediately before or after the certain step. A detection time of the lesion site as used herein may include a start time of detection of the lesion site, a display time of a notification notifying detection of the lesion site, and a time of user operation after the notification, for example.

In an embodiment, for the option inserting position, whether the option is inserted immediately before or immediately after the reference step is selected by the user. When it is desired that the steps of an option be performed as soon as possible after the lesion site is detected, the position immediately before the reference step is selected as the option inserting position. On the other hand, when it is desired that an operation and a job having been carried out already be maintained useful, the position immediately after the reference step is selected as the option inserting position. Selection as to whether the optional is inserted immediately before or immediately after the reference step may be previously made before executing the examination protocol or may be made every time a lesion site is detected.

In an embodiment, the display controller displays, before the specific option is incorporated, a first list of steps showing a plurality of steps which constitute the examination protocol and displays, after the specific option is incorporated, a second list of steps showing a plurality of steps which constitute a modified examination protocol. According to this configuration, the user becomes able to recognize contents of the modified examination protocol by viewing the second list of steps. Switching from the first list of steps to the second list of steps is performed in real time.

In an embodiment, one or more additional display elements associated with one or more additional steps constituting the specific option are distinctively represented on the second list of steps. This can facilitate recognizing an additionally inserted section (i.e., the option) in the second list of steps. Such distinctive representation is achieved by changing display forms between original display elements and the additional display elements. The one or more additional display elements may be displayed with a high luminance or with a particular hue. A mark or other indications may be placed on each of the additional display elements.

In an embodiment, the option list contains one or more option display elements representing one or more options. The display controller changes the display forms of the option display elements based on track records of selection of the options. According to this configuration, it becomes possible to select an option taking into account the track record of selection of each option. A change in the display form includes a change of a numerical value or a graphical shape contained in the option display elements, a change in size of the option display elements, a change in the hue and brightness of the option display elements, etc.

In an embodiment, the display controller changes contents of the option list based on a type of the lesion site detected by the detector. According to this configuration, a possibility of selecting an option suitable for the type of the lesion site can be increased. Conversely, a possibility of selecting an option unsuitable for the type of the lesion site can be decreased. When this configuration is employed, a detector capable of identifying the type of the lesion site is employed. In addition, an option managing table is used to manage one or more types of lesion sites targeted by the options on an option-by-option basis.

In an embodiment, the display controller displays a finding list corresponding to the specific option while the specific option is in progress, and a report creating unit is provided to create an examination report containing a particular finding selected from the finding list. When configured in this way, it becomes possible to make preparation for creating the examination report, or to perform creation of the examination report simultaneously with the ultrasound examination.

A program according to an embodiment is executed in the ultrasound diagnostic apparatus in which a series of operations including operations from transmission and reception of an ultrasound wave to display of an ultrasound image are controlled in accordance with the examination protocol composed of a plurality of steps. The program includes a detecting function, a display controlling function, and a protocol modifying function. The detecting function is a function to detect the lesion site contained in the ultrasound image while the examination protocol is running. The display controlling function is a function to display the option list showing one or more options in response to detection of the lesion site. The protocol modifying function is a function to incorporate the specific option selected from the option list into the examination protocol being run. Each of the options is composed of one or more additional steps. After the specific option is incorporated, the series of operations are controlled according to a modified examination protocol in which the specific option is incorporated.

The above-described program is designed to implement an examination protocol modifying method. The program is installed through a portable storage medium or a network into the ultrasound diagnostic apparatus as an information processor. The installed program is stored in a non-transitory storage medium.

2. Details of Embodiment

FIG. 1 shows an example of a configuration of the ultrasound diagnostic apparatus according to an embodiment. The ultrasound diagnostic apparatus is placed in a medical institution, for example, and used for conducting an ultrasound examination. Specifically, the ultrasound diagnostic apparatus is a medical device configured to form an ultrasound image based on reception signals acquired through transmission and reception of ultrasound waves.

An ultrasound probe 10 includes a transducer array composed of a plurality of transducers. The transducer array generates an ultrasound beam 12 which is electronically scanned. A beam scanning plane 14 is formed by the electronic scanning of the ultrasound beam 12. As an electronic scan mode, an electronic linear scan mode and an electronic sector scan mode, for example, have been known. A two-dimensional transducer array may be disposed in the ultrasound probe 10.

A transmitter 16 is an electronic circuit configured to supply a plurality of transmission signals in parallel with each other to the transducer array during transmission. As a result, ultrasound waves are emitted to a living body; i.e., transmission beams are formed. During reception, reflection waves reflected from the living body are received in the transducer array, and a plurality of reception signals are output in parallel from the transducer array to a receiver 18. The receiver 18 is a receiver circuit configured to process the plurality of reception signals being input in parallel, through phase alignment and addition (delay addition) for generating reception beam data.

Reception frame data is created from a plurality of sets of reception beam data arranged in an electronic scanning direction. Each set of reception beam data is composed of a plurality of sets of echo data arranged in a depth direction. A plurality of sets of reception frame data are generated through repetitive electronic scans of the ultrasound beam 12, and the generated sets of reception frame data are sent to an image generator 20.

The image generator 20 generates a plurality of sets of display frame data based on the plurality of sets of reception frame data. The image generator 20 has a coordinate converting function, a pixel interpolating function, a frame rate converting function, and other functions which are implemented by a DSC (digital scan converter), for example. Each set of display frame data corresponds to one tomographic image. The plurality of sets of display frame data output from the image generator 20 are sent via a display processor 22 to a display unit 24. The tomographic image is displayed as a moving image on the display unit 24. In a freeze state where transmission and reception of ultrasound waves are suspended, the tomographic image is displayed as a still image on the display unit 24. As other ultrasound images, a CFM image (color flow mapping image), a doppler waveform, and a three-dimensional image, for example, have been known.

The display processor 22 functions as the display controller. The display processor 22 has a function of generating various types of images including images for operation, an image merging function, a coloring function, and other functions. The display processor 22 generates, for example, a step list, an option selecting image, and the finding list, which will be described further below. The display unit 24 is a main display unit and is implemented by, for example, a liquid crystal display unit, an organic EL display unit, and the like. The image generator 20 and the display processor 22 are respectively implemented by processors, for example.

A computation controller 26 is implemented by a processor, such as a CPU, for example. In FIG. 1, a plurality of functions performed by the computation controller 26 are represented in a plurality of blocks. The computation processor 26 functions as a protocol creating unit 32, a protocol modifying unit 34, a report creating unit 36, a protocol execution controller 38, and a detector (identifying unit) 40, for example.

The protocol creating unit 32 is configured to create a plurality of examination protocols. Each of the examination protocols is composed of a plurality of steps. Each of the steps typically includes operations from an operation to establish operating conditions to an operation to store ultrasound images. The operating conditions include an operating mode (diagnostic mode), transmitting and receiving conditions, an image processing condition, and an image format, for example. The steps may include a step accompanying a measurement. The measurement as used herein includes in its scope image analysis in addition to area measurement, time measurement, and other measurement.

The plurality of examination protocols are prepared depending on contents of the ultrasound examinations, and a specific examination protocol to be used is selected from the plurality of examination protocols by the user. The use of the examination protocol can eliminate a necessity to manually set the operating conditions at the start time of execution of each of the steps. It is also possible to omit various inputs and setting operations while each of the steps is in progress. In addition, when the ultrasound examination is conducted in accordance with the examination protocol, each step can be reliably implemented, which can avoid the occurrence of a problematic omission of an ultrasound image that should be acquired. In an embodiment, each option is also created by the protocol creating unit 32.

In a case where a lesion site is detected while the examination protocol is running, the protocol modifying unit 34 incorporates an option selected by the user into the running examination protocol in accordance with a user operation to thereby modify the running examination protocol in real time. In an embodiment, a plurality of options are prepared, and an option fit for the type of a detected lesion site can be selected from the plurality of options based on a detection result. Each of the options is composed of one or more additional steps.

The protocol execution controller 38 controls a series of operations including operations from transmission and reception of ultrasound waves to display of the ultrasound image in accordance with the selected specific examination protocol. When the examination protocol is modified by incorporating an option into the examination protocol, the protocol execution controller 38 controls operations of the ultrasound diagnostic apparatus in accordance with the modified examination protocol.

The detector 40 detects a lesion site (or, more precisely, a lesion site candidate) when it emerges in a tomographic image generated as the ultrasound image, and notifies the user of an event that the lesion site is detected. In an embodiment, when the lesion site is detected, a mark encircling the detected lesion site is displayed in the tomographic image, or a mark or a character string representing the detected lesion site is displayed on a display image. Further, upon detection of the lesion site, a predetermined button is highlighted to prompt an operation to display the option list. In an embodiment, the detector 40 may further function as an identifying unit configured to identify the type of the lesion site. The contents of the option list to be presented to the user may be optimized based on the type of the lesion site.

The report creating unit 36 creates the ultrasound examination report in the form of an electronic document. To be precise, the report creating unit 36 supports user work for creating the ultrasound examination report. The ultrasound examination report includes the ultrasound image, measured values, and other items acquired in each of the steps. In an embodiment, the ultrasound examination report may further include a finding selected in each of the steps, and a schema (schematic diagram) generated in each of the steps.

An operation panel 30 is connected to the computation controller 26. The operation panel 30 includes a trackball, a plurality of switches, a keyboard, a touch screen panel 42, and other components. The touch screen panel 42 is composed of a display panel 42A and a touch panel 42B. The image for manual operation including a plurality of virtual buttons is displayed on the display panel 42A. Manual operations performed on the plurality of virtual buttons are detected through the touch panel 42B. The image for manual operation is generated by the display processor 22 under control by the computation controller 26.

A storage 28 is connected to the computation controller 26. The storage 28 is implemented by a semiconductor memory, or a hard disk, for example. The storage 28 stores a protocol information group 44, an option information group 46, a protocol managing table 48, an option managing table 50, and other data.

The protocol information group 44 is composed of a plurality of sets of protocol information 44A created by the protocol creating unit 32. Modified protocol information may be contained in the protocol information group 44. Each set of the protocol information 44A includes a plurality of control data items needed to perform the plurality of steps constituting the examination protocol.

The option information group 46 includes a plurality of sets of option information 46A generated by the protocol creating unit 32. Each set of the option information 46A is composed of one or more control data items needed to perform one or more additional steps constituting the option.

The protocol managing table 48 is provided to manage the examination protocols associated with the sets of the protocol information 44A in the protocol information group 44. The option managing table 50 is provided to manage the options associated with the sets of option information 46A in the option information group 46. The storage 28 further stores a finding managing table, a scheme managing table, and other data, which are not illustrated in FIG. 1.

FIG. 2 shows an example of the protocol information. The protocol information 44A shown in FIG. 2 includes a protocol ID 52, a protocol name 53, and a plurality of sets of step information 54, for example. Each set of the step information 54 includes a step number 55, a step name 56, operating conditions 57, and other items. The operating conditions include the apparatus operating mode, a transmission frequency, a transmission pulse repetition frequency, a gain, . . . , a displaying condition, etc. The step information 54 may include information related to measurement. Implementation of each step is controlled with reference to a corresponding set of step information 54.

FIG. 3 shows an example of the option information. The option information 46A shown in FIG. 3 includes an option ID 58, an option name 59, and a plurality of sets of additional step information 60, for example. Each set of the additional step information 60 includes a step number 61, a step name 62, and operating conditions 63. Implementation of each additional step is controlled with reference to a corresponding set of the additional step information 60.

FIG. 4 shows an example of the protocol managing table. The protocol managing table 48 shown in FIG. 4 is composed of a plurality of records 68 associated with the plurality of examination protocols. Each of the records 68 includes a protocol ID 70 and an information item 72 for identifying a medical division (an examination site). With reference to the information item 72, the medical division or the examination site to which the examination protocol should be applied can be identified.

FIG. 5 shows an example of the option managing table. The option managing table 50 shown in FIG. 5 is composed of a plurality of records 76 associated with the plurality of options. Each of the records 76 includes an option ID 78, an information item 80 for identifying the medical division (examination site), and an information item 82 for identifying the types of lesion sites. With reference to the information item 82, the type of the lesion site corresponding to the option can be identified.

Figure 6:
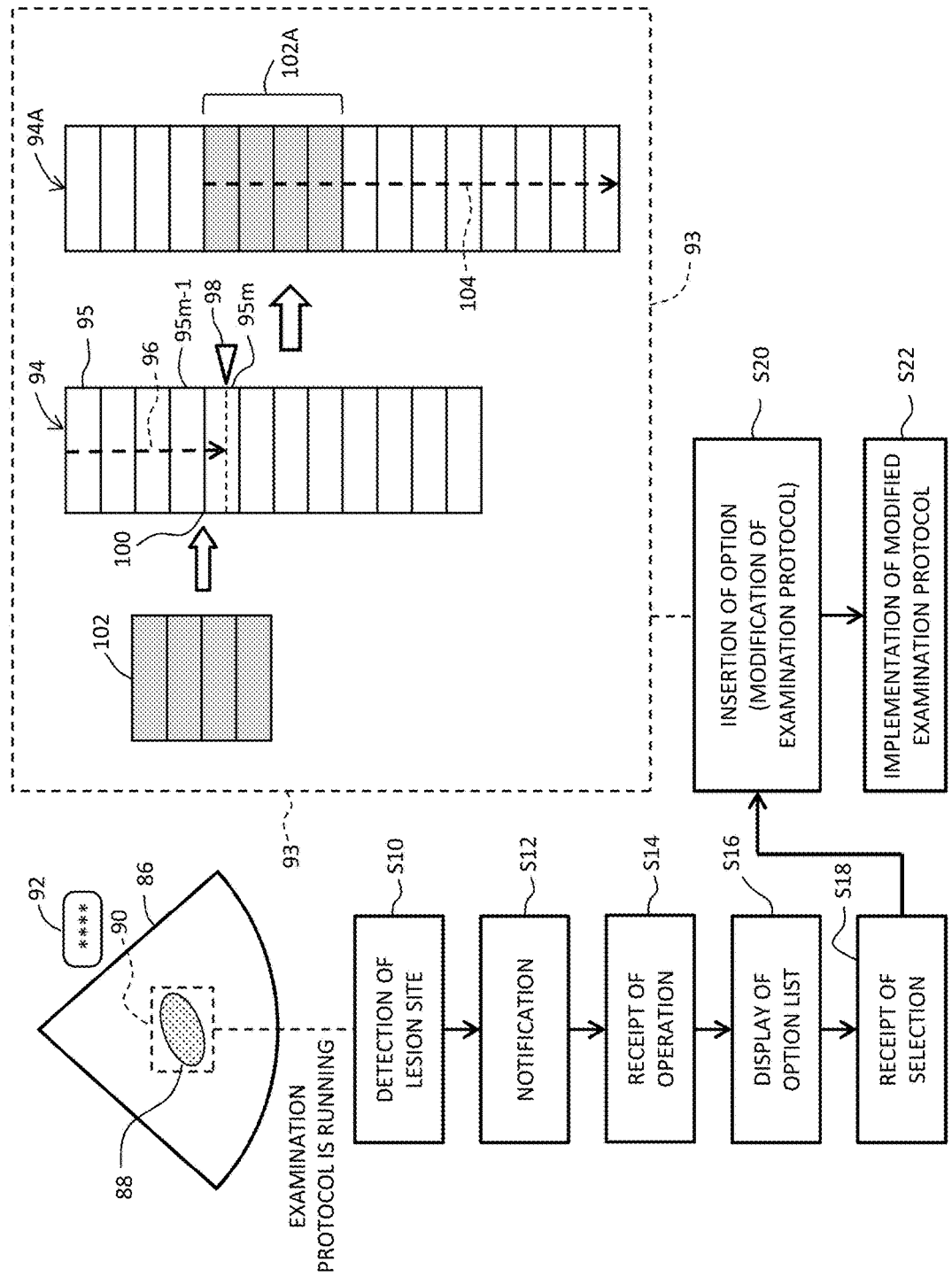
FIG. 6 schematically shows an example of operations (or actions)

FIG. 6 schematically shows an operating method according to an embodiment. The diagram illustrated in FIG. 6 shows actions of the above-described computation controller and display processor. When a lesion site 88 emerges in a tomographic image 86 while a specific examination protocol is running, the lesion site is detected in step S10. As a result, for example, a mark 90 encircling the lesion side is displayed, or a display element 92, such as text or graphics, representing detection of the lesion site is displayed close to the tomographic image 86. At this time, an identified type of the lesion site may be additionally displayed.

In step S12, a predetermined button displayed on the touch screen panel is emphasized in response to detection of the lesion site, to notify the user of the detection of the lesion site. Here, the button is highlighted or flashed, for example. When the button is operated by the user, the user operation is received in step S14. In step S16, an option list is displayed on the touch screen panel. The option list includes the one or more display elements representing the one or more options.

When the user operates a specific display element; i.e., when a specific option is selected, the selection by the user is received in step S18. In step S20, the selected option; i.e., one or more additional steps, is incorporated into the examination protocol which is running. In this way, the running examination protocol is modified in real time. At the time of modification, items in the displayed step list are simultaneously modified. Specifically, a first list of steps being an unmodified list is switched in real time to a second list of steps being a modified list. In step S22, the modified examination protocol is executed.

FIG. 6 schematically shows a process (see reference numeral 93) of modifying the examination protocol that is performed in step S20. An examination protocol 94 having been originally selected consists of a plurality of steps 95 which are lined up in a time series. In the illustrated example, a mark 98 indicates a present time, and an arrow 96 indicates progress of the examination protocol up to the present time. In a case where a lesion site is detected in the course of a step 95$m$, and a specific option 102 is selected from the option list, the specific option 102 is inserted at a position 100 between the step 95$m$, which includes the present time being a detection time of the lesion site, and a step 95$m$-1 previous to the step 95$m$. That is, the option 102 is inserted immediately before the step 95$m$. In this way, a modified examination protocol 94A in which the option 102A is incorporated is generated. After the option 102A is incorporated, a series of the steps are sequentially carried out, starting from an initial step in the option 102A as indicated by an arrow 104.

In the example shown in FIG. 6, the option is inserted immediately before the reference step including the detection time of the lesion site (immediately preceding mode), while the option may be inserted immediately after the reference step (immediately following mode). The immediately preceding mode can enable an early start of the option suitable for the lesion site existing at present. The immediately following mode can prevent waste of operation or work which has already been conducted in the presently ongoing step. It is also possible to insert the option at some point into the reference step itself (partway mode). However, in this case, because the reference step is divided into two sections, the partway mode is apt to raise problems, such as deterioration in operability, or confusion about operation, for example. Therefore, it is desirable to adopt either the immediately preceding mode or the immediately following mode. In an embodiment, a selection of the immediately preceding mode or the immediately following mode to be adopted may be performed by the user in advance or at the time of selecting the option.

Figure 7:
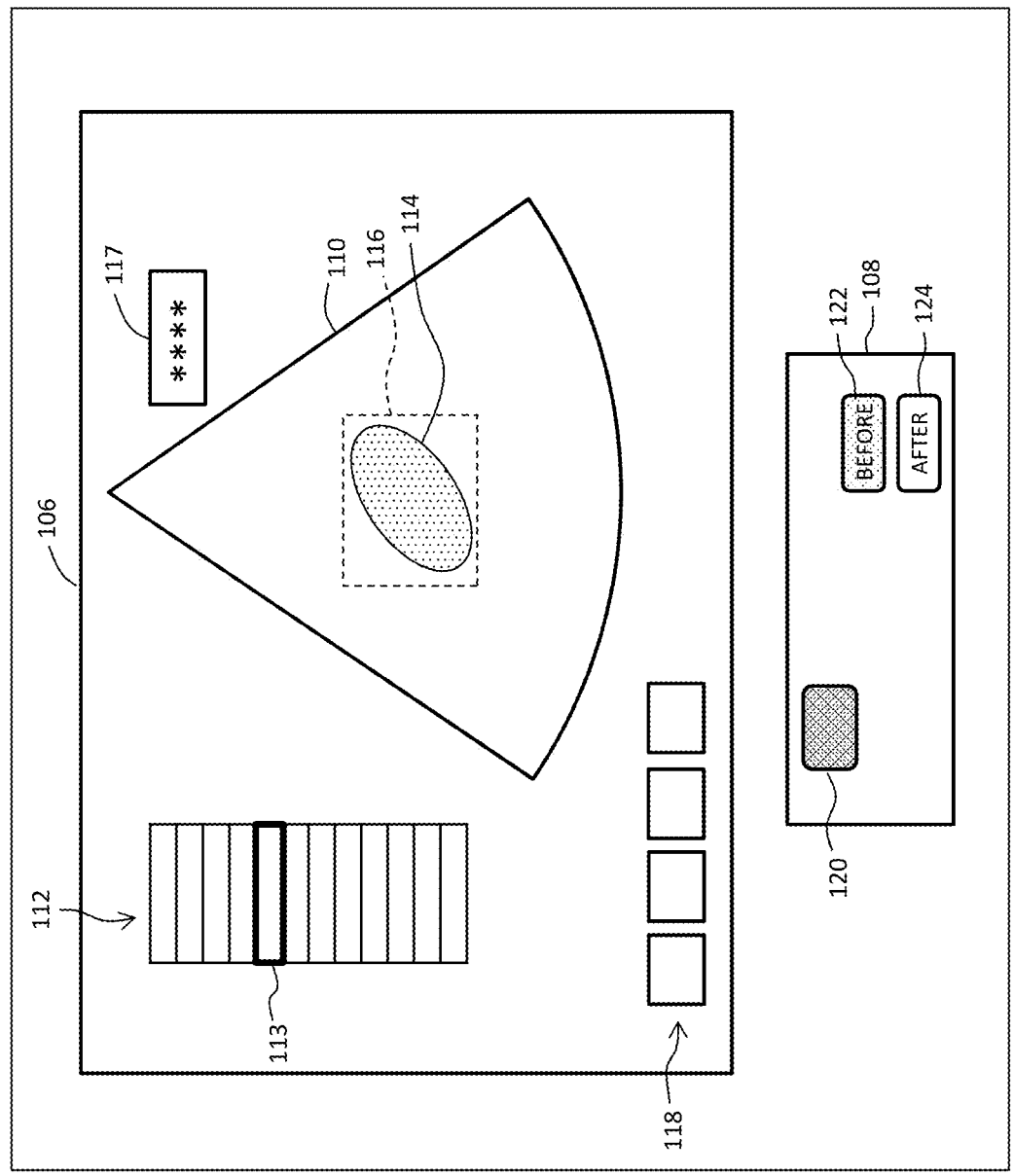
FIG. 7 shows a first display example.

The operations according to the embodiment will be specifically explained with reference to FIGS. 7 to 11. FIG. 7 shows a first display example.

A display image 106 displayed on the main display unit contains a tomographic image 110 and a step list 112. The step list 112 consists of a plurality of rows representing a plurality of steps. The row corresponding to the presently ongoing step is highlighted (see reference numeral 113). A lesion site 114 emerging in the tomographic image 110 is automatically detected, and a mark 116 is accordingly displayed. An information item 117 representing a type of the lesion site is also displayed. The display image 106 further contains a plurality of images 118 acquired and stored through the steps having been executed already. Each of the plurality of images 118 is a downsized image; i.e., a thumbnail.

A display image 108 displayed on the touch screen panel contains a virtual button (option launch button) 120. The option launch button 120 is highlighted or flashed in response to detection of the lesion site 114. The display image 108 further includes a virtual button 122 used for selecting the immediately preceding mode and a virtual button 124 used for selecting the immediately following mode. For example, the button 112 may have been selected in an initial state, while the button 124 may be operated as needed. When the option launch button 120 is operated, a below-described display image is displayed.

Figure 8:
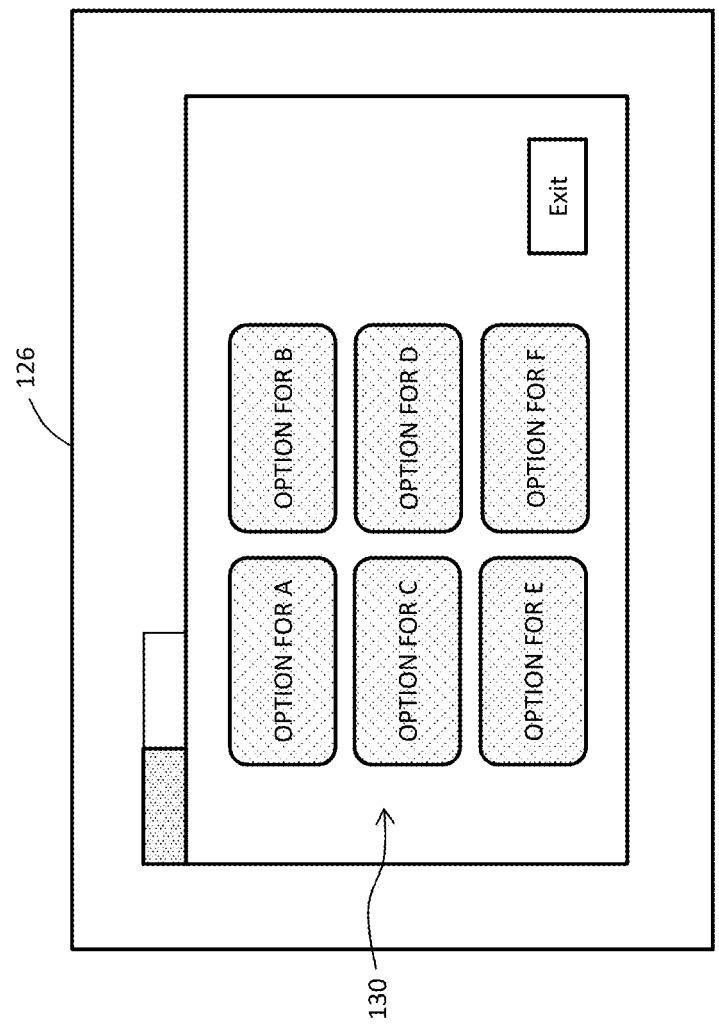
FIG. 8 shows a first example of an option list.

FIG. 8 shows a display image 126 displayed on the touch screen panel. The display image 126 contains an option list 130 according to the first display example. The option list 130 is composed of a plurality of virtual buttons representing a plurality of options. The virtual buttons are assigned to the options in a one-to-one relationship. A desired option can be launched by operating the virtual button assigned to the desired option. The display image 126 may further contain a pair of buttons for selecting the immediately preceding mode and the immediately following mode.

FIG. 9 shows a state in which an option is incorporated. A display image 132 displayed on the main display unit contains a tomographic image 134 and a step list 136. The step list 136 is designed to represent an examination protocol in which the option is incorporated; that is, the modified examination protocol. The initially displayed step list is switched to a modified step list at a time when the option is incorporated.

The step list 136 is composed of a plurality of rows representing a plurality of steps in which a block of rows corresponding to the option is identifiably displayed. For example, the block is displayed with high brightness or by means of a predetermined hue. A predetermined mark may be placed on each of the rows contained in the block. This can allow the user to easily identify an added section in the modified examination protocol. A highlighted row 138 represents a presently ongoing step at the present time.

The display image 132 contains a plurality of downsized images 142 respectively representing a plurality of tomographic images having been acquired and stored by carrying out a plurality of steps. Among the downsized images 142, downsized images 144$a$, 144$b$, and 144$c$ having been acquired and stored by executing the option are distinctively displayed. Such distinctive display allows the user to properly recognize that the downsized images 144$a$, 144$b$, and 144$c$ are acquired by way of exception. The downsized images 144$a$, 144$b$, and 144$c$ may be distinctively displayed by coloring their frames with a predetermined hue.

FIG. 10 shows an option list 148 according to a second display example. The option list 148 is composed of a plurality of virtual buttons respectively representing a plurality of options. Each of the virtual buttons has a numeric label 150. The numeric label 150 indicates the number of previous selections of the corresponding option; i.e., a track record of selections of the corresponding option. Such information can be referenced to select a specific option.

FIG. 11 shows an option list 152 according to a third display example. The option list 152 is composed of a plurality of virtual buttons respectively representing a plurality of options. The virtual buttons include a button 154$a$ having a large size and a button 154$b$ having a small size. That is, the size of each button reflects the track record of previous selections of the button. A button associated with an option, whose number of selections is great, may be shown with an increased size, which can facilitate preferential selection of the option corresponding to the button of the increased size. Another property of the buttons may be varied depending on values of the track record of previous selections.

Next, creation of an ultrasound examination report and support for the creation will be explained with reference to FIGS. 12 and 13.

A display image 156 shown in FIG. 12 contains a tomographic image 158, a step list 160, and a pop up window 166. As indicated by reference numeral 174, a measurement has already been conducted on the tomographic image 158, and a numerical value 176 obtained by the measurement is displayed. A section 162 in the step list 160 corresponds to an option. A step corresponding to a row 164 is a presently ongoing step. The ongoing step is contained in the option.

The pop up window 166 is displayed in response to a predetermined user operation. A finding list 168 for the option is contained in the pop up window 166. Specifically, correlations between options and types of lesion sites are managed, and the finding list 168 fit for the type of a detected lesion site is displayed based on the correlation. The finding list 168 includes a plurality of selectable findings. As indicated by reference numeral 170, a selection of a specific finding can be performed through an operation of a check box. As a result of the operation, the selected specific finding is displayed as a character string 172 on the tomographic image 158. Then, the displayed character string is also stored along with the tomographic image when the tomographic image is stored. In addition, the selected specific finding is included along with the tomographic image in an ultrasound examination report.

The pop up window 166 includes a virtual button 178 for launching a scheme creation tool. When the button 178 is operated, another pop up window, which will be explained below, is displayed.

Figure 13:
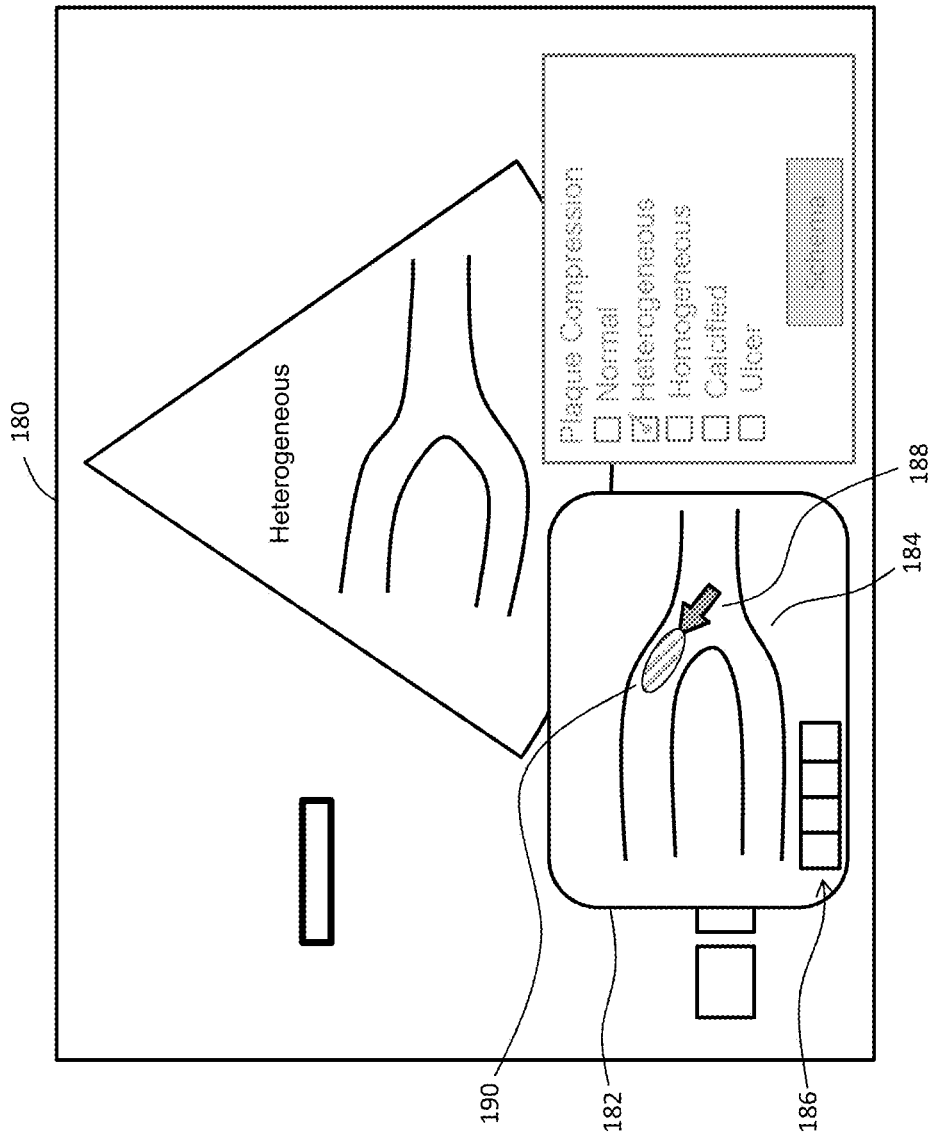
FIG. 13 is a diagram for explaining a schema creation tool.

As shown in FIG. 13, a pop up window 182 is a schema creation window including a basic graphical shape 184. In the schema creation window, for example, a freehand graphical shape can be added to the basic graphical shape 184 using a pointer 188. For example, a graphical shape 190 representing a position and a size of a plaque may be added. A button array 186 is composed of a plurality of virtual buttons respectively associated with a plurality of functions that are used when a schema is created. The virtual buttons include a button for selecting a size, a type, and other properties of line, a button for launching an eraser, a reset button, and other buttons. The schema created on the pop up window 182 is inserted into the ultrasound examination report. In an embodiment, a basic graphical shape corresponding to an option; i.e., a type of the lesion site, is displayed on the pop up window.

The load of creating the examination report can be greatly lightened by supporting, as described above, selection of the finding and creation of the schema based on the option while the examination protocol is running. The finding list may be displayed and/or the schema creation tool may be used, when any normal steps other than the steps in the option are in progress.

Figure 14:
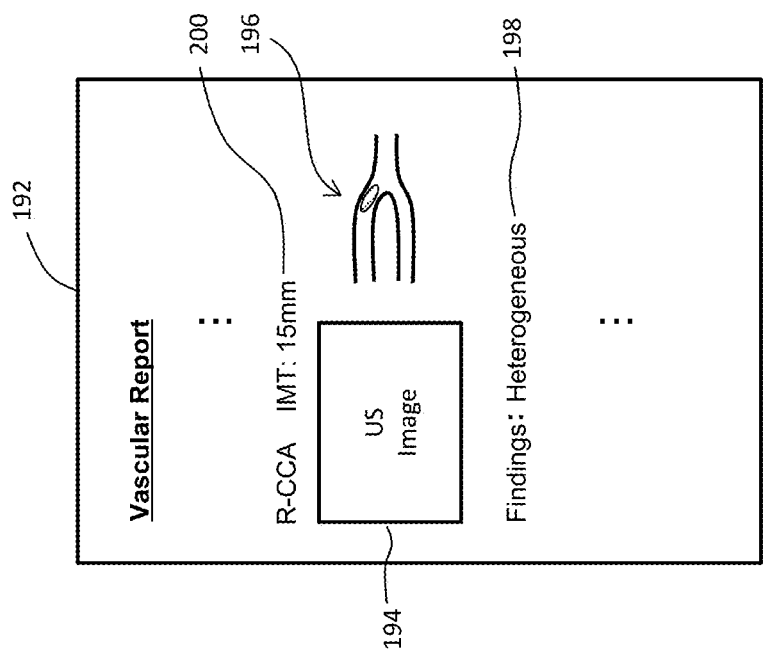
FIG. 14 shows an example of an examination report.

FIG. 14 shows an example of the ultrasound examination report. An ultrasound examination report 192 shown in FIG. 14 includes an ultrasound image 194 and a measurement value 200 obtained when the option is executed. In addition, the ultrasound examination report 192 further contains a character string 198 representing a finding selected when the option is executed and a schema 196 created when the option is executed.

Figure 15:
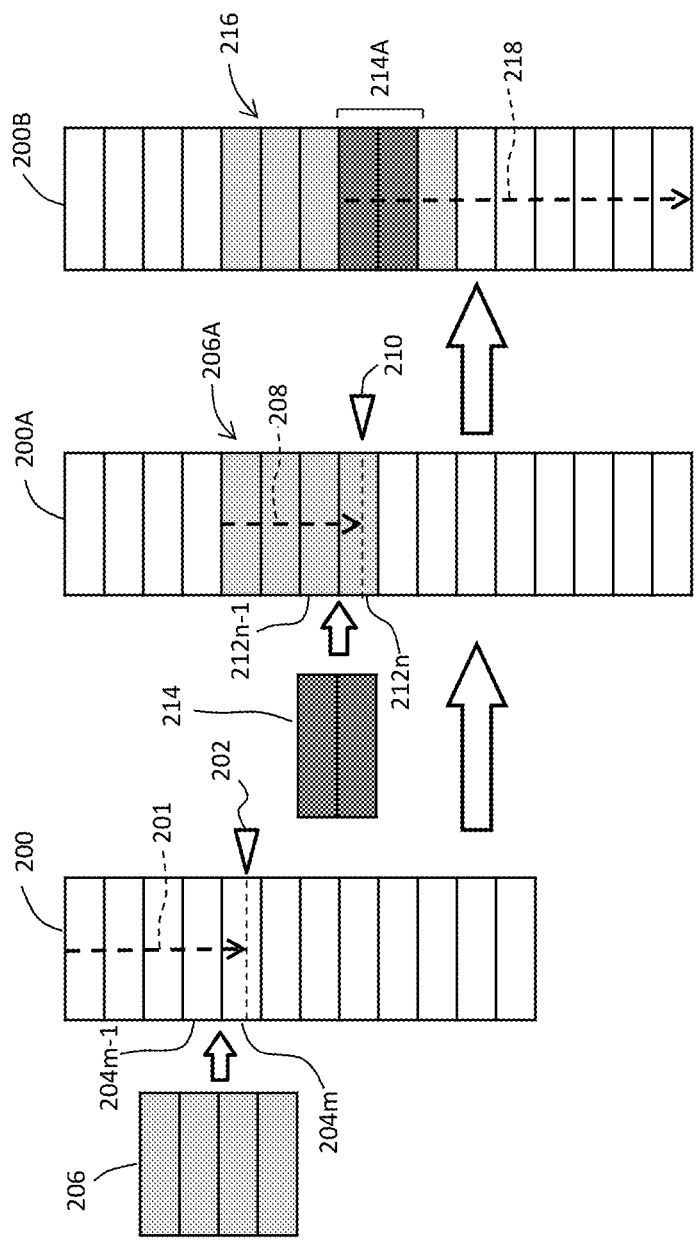
FIG. 15 shows a first example of an option inserting method.

Referring next to FIGS. 15 and 16, an exceptional operation will be explained, the operation being taken when another lesion site is detected during execution of an option. FIG. 15 shows a combination of the immediately preceding mode and the immediately preceding mode, and FIG. 16 shows a combination of the immediately preceding mode and the immediately following mode. It should be noted that in FIGS. 15 and 16, the same components as those illustrated in FIG. 6 are designated by the same reference numerals as those in FIG. 6, and the descriptions related to the components will not be repeated.

In FIG. 15, an option 206A is carried out that is incorporated, as indicated by an arrow 208, in a modified examination protocol 200A. Specifically, at the present time 210, a step (reference step) 212$n$ is in progress. When another lesion site is detected in the course of the step 212$n$, and an option 214 is selected in response to the detection, the selected option 214 is inserted between the step 212$n$ and its previous step 212$n$-1; i.e., immediately before the step 212$n$ (immediately preceding mode). As a result, a further modified examination protocol 200B in which the option 214A is incorporated in the option 216 is created. After the two options are incorporated in the further modified examination protocol 200B, starting from an initial step in the newly added option 214A, a plurality of steps are sequentially carried out as indicated by an arrow 218. In this way, the options are nested in the operation example illustrated in FIG. 15.

In FIG. 16, when the lesion site is detected at the present time 210, and the option 214 is selected, the selected option 214 is inserted immediately after the step (reference step) which is ongoing at the present time 210. As a result, the further modified examination protocol 200B in which the option 214B is incorporated subsequent to an option 222 is created. In the further modified examination protocol 200B, as indicated by an arrow 224, the option is carried out after processing in the reference step is completed. As such, in the operation example shown in FIG. 16, the option is incorporated following the previous option, so that the two options are successive.

As has been described above, when a lesion site emerges, the contents of the examination protocol can be modified easily and appropriately based on the lesion site according to the embodiment. In this way, examination of the lesion site can be reliably conducted, while the burden on a medical examiner can be alleviated.

The invention claimed is:

1. An ultrasound diagnostic apparatus, comprising:
a processor configured to control a series of operations in accordance with an examination protocol composed of a plurality of steps, the series of operations comprising operations from transmission and reception of an ultrasound wave to display of an ultrasound image, the processor being further configured to:
detect a lesion site contained in the ultrasound image while the examination protocol is running;
control an operation to display an option list showing one or more options in response to detection of the lesion site;
incorporate a specific option selected from the option list into the examination protocol being run, each of the one or more options in the option list including one or more additional steps;
control the series of operations in accordance with a modified examination protocol in which the specific option is incorporated;
identify, as a reference step, a step that is ongoing at a time of detection of the lesion site; and
determine, as an option inserting position where the specific option is inserted into the examination protocol being run, a position immediately before or immediately after the reference step, wherein when the position immediately before the reference step is determined as the option inserting position, the reference step is carried out again.

2. The ultrasound diagnostic apparatus according to claim 1, wherein whether the option inserting position is immediately before or immediately after the reference step is selected by a user.

3. The ultrasound diagnostic apparatus according to claim 1, wherein the processor is further configured to:
control, before incorporating the specific option, an operation to display a first step list showing a plurality of steps constituting the examination protocol; and
control, after incorporating the specific option, an operation to display a second step list showing a plurality of steps constituting the modified examination protocol.

4. The ultrasound diagnostic apparatus according to claim 3, wherein one or more additional display elements associated with the one or more additional steps constituting the specific option are distinguishably displayed in the second step list.

5. The ultrasound diagnostic apparatus according to claim 1, wherein:
the option list comprises one or more option display elements representing one or more options; and
the processor is further configured to control an operation to change a display form for each of the one or more option display elements based on a track record of selection of each of the one or more options.

6. The ultrasound diagnostic apparatus according to claim 1, wherein:
the processor is further configured to control an operation to change contents of the option list based on a type of the lesion site detected.

7. The ultrasound diagnostic apparatus according to claim 1, wherein the processor is further configured to:
control an operation to display a finding list fit for a type of the detected lesion site, for the specific option while the specific option is in progress; and
create an examination report which contains a particular finding selected from the finding list.

8. A program executed in an ultrasound diagnostic apparatus wherein a series of operations are controlled in accordance with an examination protocol composed of a plurality of steps, the series of operations comprising operations from transmission and reception of an ultrasound wave to display of an ultrasound image, the program comprising:
a function of detecting a lesion site contained in the ultrasound image while the examination protocol is running;
a function of controlling an operation to display an option list showing one or more options in response to detection of the lesion site; and
a function of incorporating a specific option selected from the option list into the examination protocol being run, each of the one or more options including one or more additional steps;
a function to control the series of operations in accordance with a modified examination protocol in which the specific option is incorporated;
a function to identify, as a reference step, a step that is ongoing at a time of detection of the lesion site; and
a function to determine, as an option inserting position where the specific option is inserted into the examination protocol being run, a position immediately before or immediately after the reference step,
when the position immediately before the reference step is determined as the option inserting position, operations in accordance with the modified examination protocol being sequentially carried out, commencing with carrying out the reference step again.

9. The program according to claim 8, wherein the program executed in the ultrasound diagnostic apparatus further comprises:
a function to control, before incorporating the specific option, an operation to display a first step list showing a plurality of steps constituting the examination protocol; and
a function to control, after incorporating the specific option, an operation to display a second step list showing a plurality of steps constituting the modified examination protocol.

10. The program according to claim 8, wherein the program executed in the ultrasound diagnostic apparatus further comprises a function to control an operation to change contents of the option list based on a type of the lesion site detected.

11. The program according to claim 8, wherein the program executed in the ultrasound diagnostic apparatus further comprises:
a function to control an operation to display a finding list fit for a type of the detected lesion site, for the specific option while the specific option is in progress; and
a function to create an examination report which contains a particular finding selected from the finding list.

12. The ultrasound diagnostic apparatus according to claim 1, wherein when the position immediately before the reference step is determined as the option inserting position, operations in accordance with the modified examination protocol are sequentially carried out, commencing with carrying out the reference step again.

* * * * *